United States Patent [19]

Maxey et al.

[11] 4,351,029

[45] Sep. 21, 1982

[54] TOOL LIFE MONITORING AND TRACKING APPARATUS

[75] Inventors: Robert E. L. Maxey, North Huntington; James N. Brecker, Pittsburgh, both of Pa.

[73] Assignee: Westinghouse Electric Corp., Pittsburgh, Pa.

[21] Appl. No.: 100,674

[22] Filed: Dec. 5, 1979

[51] Int. Cl.³ .................... G06F 15/46; G01N 19/02
[52] U.S. Cl. .................................. 364/511; 73/104; 340/680; 408/11; 364/474
[58] Field of Search ............... 364/474, 475, 105, 119, 364/506, 511, 483, 550; 340/679, 680; 318/571, 563, 565, 39, 650, 561; 409/145, 148, 150, 151, 153, 154, 156, 80; 408/9, 10, 11, 12, 13, 16; 324/142, 76 A; 73/104, 105, 117, 117.3, 117.4, 116

[56] References Cited

U.S. PATENT DOCUMENTS

| | | | |
|---|---|---|---|
| 3,220,315 | 11/1965 | Mathias | 409/148 |
| 3,555,516 | 1/1971 | Proctor | 364/107 X |
| 3,571,834 | 3/1971 | Mathias | 408/9 |
| 3,667,290 | 6/1972 | Hohn | 73/116 |
| 3,681,978 | 8/1972 | Mathias et al. | 73/660 |
| 3,809,870 | 5/1974 | Auble et al. | 364/511 |
| 3,839,628 | 10/1974 | Higgins et al. | 364/511 X |
| 3,991,984 | 11/1976 | Porter | 364/511 X |
| 4,031,368 | 6/1977 | Colding et al. | 364/105 |
| 4,090,403 | 5/1978 | Tsukada et al. | 73/104 |
| 4,207,567 | 6/1980 | Juengel et al. | 73/104 X |
| 4,208,718 | 6/1980 | Chung | 364/474 |

*Primary Examiner*—Joseph F. Ruggiero
*Attorney, Agent, or Firm*—C. M. Lorin

[57] ABSTRACT

Net power consumed by one or more tools, continuously or intermittently is totalized and compared with a predetermined energy limit characterizing the life expectancy of a tool for optimum and safe use on a machine tool. Digital and computer techniques are used in order to keep track of the usage of the various tools within their respective life expectancies.

7 Claims, 10 Drawing Figures

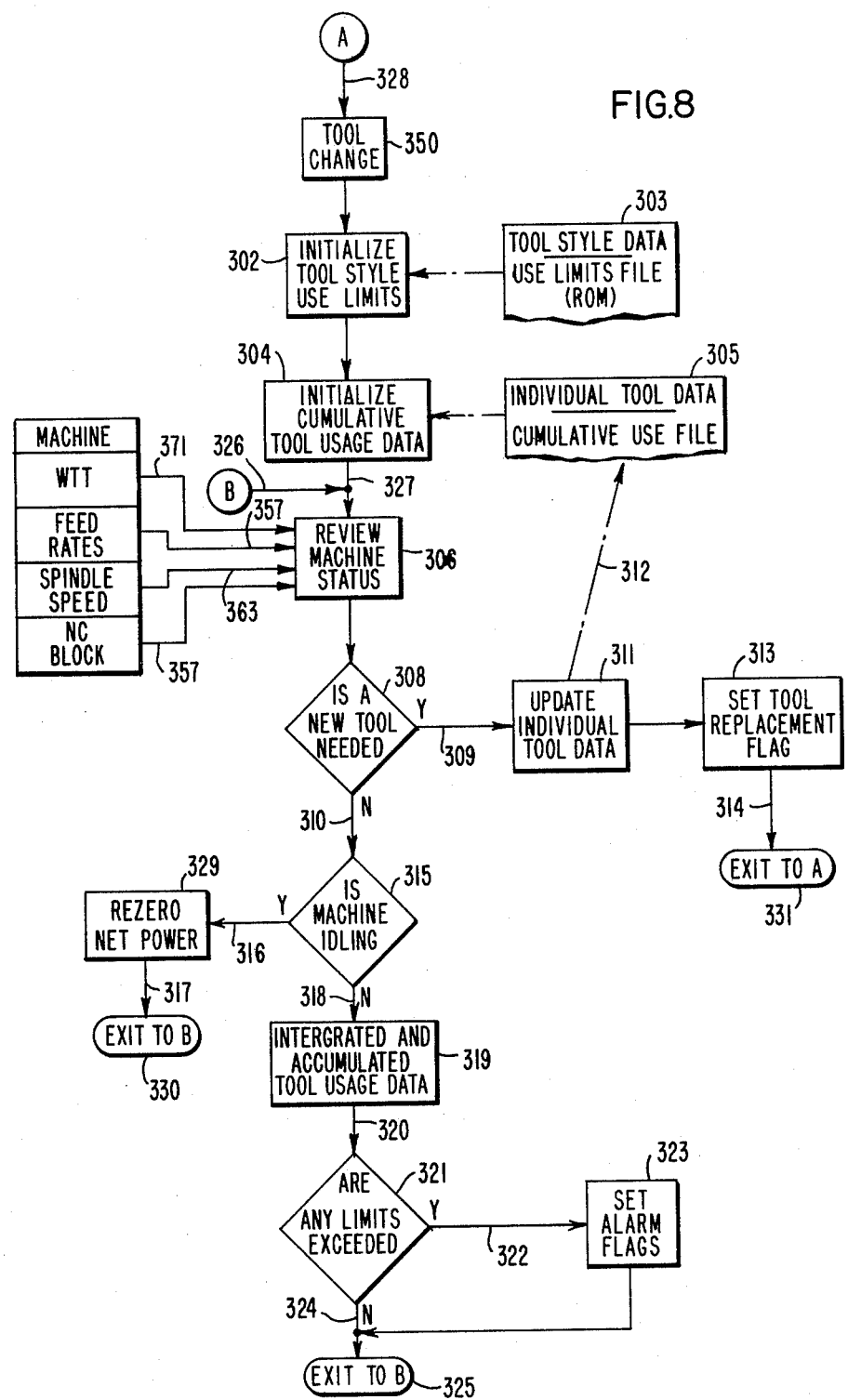

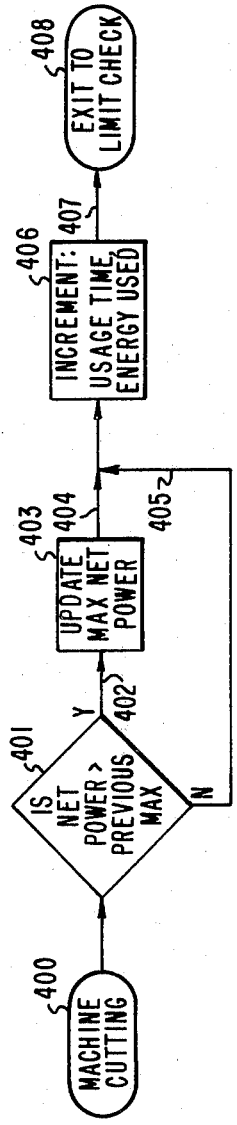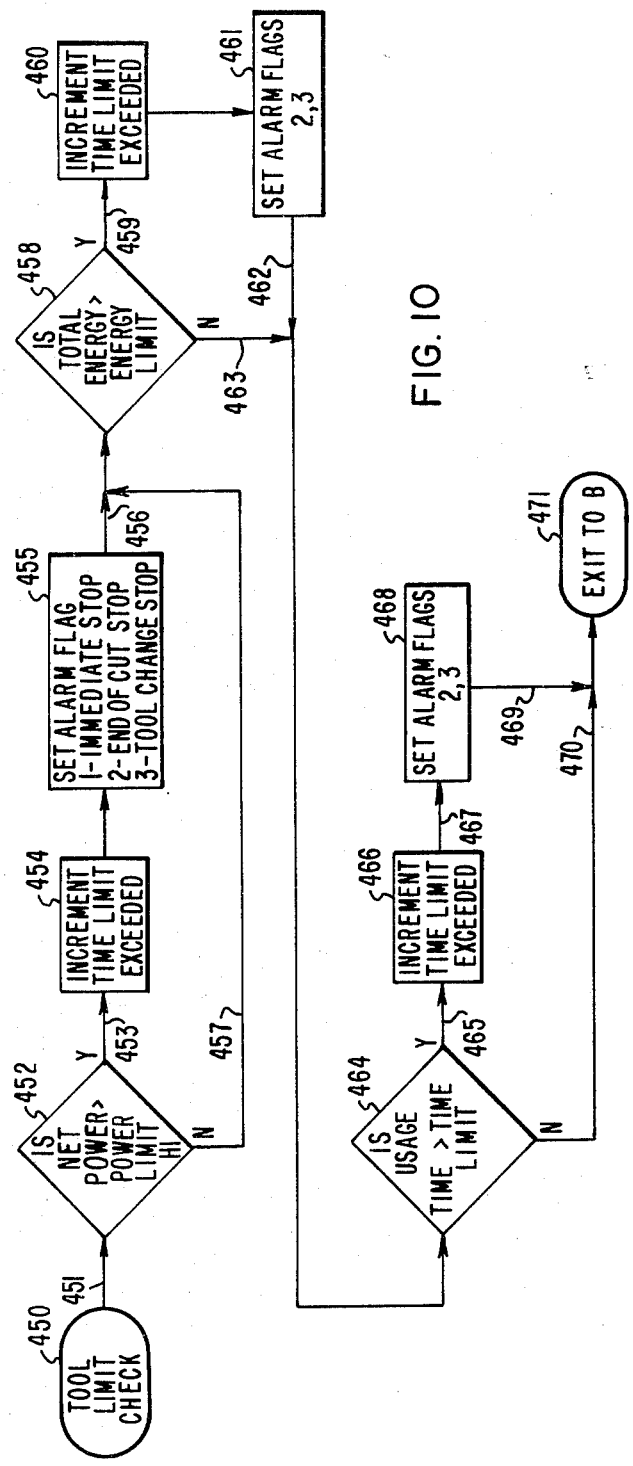

TOOL LIFE MONITORING AND TRACKING APPARATUS

BACKGROUND OF THE INVENTION

The present invention relates to method and apparatus for monitoring the quality of a tool on machine tool. Obtaining an optimum tool life e.g., a maximum volume of metal removed by the tool before resharpening, has been a problem of great concern in the industry for many years. Since excessive tool wear lead to high forces on the tool and this causes tool failure and interruption of production, it has been the practice to change the tools before this happens, thus, long before their useful life has been reached.

In order to cope with this problem, machines have been developed in which machining power is monitored while the feed rate under the tool is being controlled, so as to get fuller use out of the tools before they are resharpened. Thus, power as applied to the machine tool appears to be indicative of the cutting force exerted by the tool in operation. Power adaptive control may be used concurrently. After the machine spindle power has been initially established at a preset level, the table feed is automatically increased, or decreased, depending upon whether the machine power is below, or above, the preset power value. In one embodiment, an analog circuit establishes what the spindle power at a given instant actually is. The machine operator increases a potentiometer setting during cutting until, from direct observation, the tool appears to be becoming overloaded at which time the power level being reached is taken as the preset level. Thereafter, whenever the spindle power exceeds the preset level, that is when the tool encounters excessive uncut material, the table feed will be slowed down in order to restore the preset level. Conversely, should the tool start cutting lightly due to less material being in its path, then control will increase the table speed, thus maintaining the same preset level. See, for instance, U.S. Pat. No. 3,571,834 of Richard A. Mathias.

While this mode of power adaptive control works reasonably well for repeated rough cuts of the same geometry, with light finish cuts, characteristically, the control becomes less effective. In such case, the operator's setting for total power is only slightly greater than idle power, for instance 2.1 HP as compared to 2.0 HP. The operator could detect, by direct observation of the cutting, that a poor chip is being cut for the given spindle rpm. He would then decrease or increase spindle speed by the slight amount of control necessary to improve the chip quality. Unfortunately, when controlling the tool operation in this fashion, any change of spindle speed will also cause a change in idle power. Since the total power remains the same, the tool will in fact now cut heavier or lighter chips. The consequence will be that the tool can break, in the first alternative, or it will not cut at all, in the second alternative.

The improvement according to the present invention resides in providing means for automatically compensating for changes in the power required to idle the spindle. This makes the adaptive control easier to program and easier to use. The machine operator will no longer need to adjust the setting of the potentiometer as frequently. A direct consequence of such automatic compensation is to enable a numerical control (NC) programmer or a manufacturing engineer (ME) to calculate automatically the desired cutting power setting and readily set the potentiometer or digital setting accordingly, thus, without having to compensate for the resulting changes in idle power. This improvement is achieved by analog or digital means. When idle power compensation is achieved by analog means, a bias signal is supplied so as to nullify the output of the power transducer of the spindle motor when the spindle is turning at idle speed. Once the spindle is turning under load, the bias no longer matches the transducer output, and net power is derived which is used to monitor the tool sharpness or which can be applied within an adaptive control process. Where digital means obtain, a latch or memory circuit is used to store the output of the power transducer of the spindle motor while under idle conditions. Once the tool is in operation, the excess of power is obtained by subtracting the stored value from the transducer output, thereby to derive net power.

It is known from U.S. Pat. No. 3,220,315 of R. A. Mathias to derive an indication of the spindle torque after signal compensation in order to balance out spindle idle conditions. It is also known from U.S. Pat. No. 3,681,978 of R. A. Mathias, et al. to measure the external load applied to the tool by subtraction of idle conditions.

These techniques, however, are complicated and costly. Moreover, they are not conducive to full digital treatment as desirable with modern computerized numerical control. The preferred embodiment of the present invention approaches the problem of attaining a true and usable representation of the force exerted by the tool on the workpiece with its cutting edge at any torque-level or spindle speed, by using different parameters. Instead of using actual forces, as translated for instance into a mechanical deflection of the tool, or of inferring the torque from a consideration of spindle speed, it is proposed to use the electrical parameters of the power supply, namely voltage, current and phase angle (the latter where alternating current is involved) so as to directly derive an indication of the energy consumed both under cutting operation and under idle conditions. Net power, obtained by subtraction of an offset representing idle power, is taken as an indication of the amount of force developed at the interface of the tool with the workpiece. It is true that total power has been recognized in the prior art as indicative of the work done by the tool. However, total power has not been understood in the past as anything other than a related factor, and a practical determination of the force exerted by the tool has always called for sensors or other electromechanical devices for correlating parameters such as torque, speed, temperature, deflection, ...

Thus, power monitoring is effective to indicate the degree of wear in many situations, especially when the tool is used under closely controlled and identical cutting conditions. More sophistication is involved when the tool is used at several different occasions and under different successive machining operations. Still, it appears desirable and even necessary, when a major requirement is to ensure with a machine tool and optimum tool life, to determine wear of a tool as it occurs and in each situation to be able to ascertain whether tool failure is impending.

In accordance with the present invention, it is proposed to integrate the power consumed by a tool e.g., to derive an indication of the energy used by the tool over its lifetime. This concept is based on a formula, known in abrasive wear theory, relating the wear volume V to the load P and the sliding distance L of the tool to the workpiece, as follows:

$$V = K \cdot P \cdot L \qquad (1)$$

where K is a constant determined by chemistry, hardness, and other factors involving the tool and the workpiece. While P times L is equal to the work done, or the energy put into the wear process, it is conceivable that the wear volume should be proportional to the integrated power used in the wear process. Thus:

$$V = K_2 \int (\text{net power}) \, dt \qquad (2)$$

Since the wear process may be somewhat sensitive to temperature and other parameters, equation (2) is an approximation. Nevertheless, it is found to be a good approximation. This formula also provides a good basis for further refinements. While constant K in formula (1) depends upon several factors affecting the tool and the workpiece, formula (2) is not so dependent and therefore is applicable to several different cutting situations. Moreover, equation (2) follows very advantageously from the aforementioned net power monitoring concept. Since net power monitoring rests upon the elimination of spindle idle power as a factor, net power which is the key parameter indicative of wear, can be integrated up to any given time and if such instantaneous integrations are effected at different successive time intervals and under successive different cutting situations, it becomes possible to keep track and continuously monitor wear, thereby to derive an overall tool wear indication. Equation (2) is also applicable to implementations other than through a direct derivation of net power electrically, where an indication of power is to be integrated with time. Thus, other known techniques for the determination of energy expanded through the tool can be used as a basis for integration under equation (2).

In accordance with the present invention, monitoring of the tool life is accomplished by combining in a machine tool (1) net power monitoring and (2) computerized machine control system. The net power monitor unit supplies a parameter to be processed for each tool while the computer unit associated with the machine tool keeps track of the accumulated usage for each of a plurality of tools and stands ready to give a warning message whenever a particular tool has to be replaced.

The net power circuit provides an instantaneous analog signal output proportional to the total power. A voltage-to-frequency converter generates a pulse train, the frequency of which is proportional to the total spindle power. Up/down counter means and offset storage means concur in providing a pulse signal having a frequency which is proportional to net power; e.g., cutting power. The pulse signal is accumulated in a counter. The computer unit automatically resets the counter to zero if another tool has to be inserted in the machine spindle, while the accumulated count is being held in reserve for later use as an initial count if the original tool is being put again into use on the machine. When resetting the counter, the offset storage is also reset if spindle speed and the tool have both been changed. Thus, the computerized control unit monitors the total accumulated pulse count for all tools used. A warning light, or buzzer, will be actuated whenever a tool has reached its total allowable count; e.g., an empirically predetermined optimum tool life. Should a tool be changed before it reaches such allowed total usage, the computerized control unit will do the bookkeeping, retaining count data and adding more in each instance to the past accumulated total for future use of the tool.

Moreover, a maximum allowable cutting power, or accumulated count, is assigned to each tool, which will trigger the warning and can bring about an immediate tool replacement. When such maximum is conservatively chosen, any unforeseen "catastrophic" situation due to excessive wear, can be avoided.

The invention also provides for additional refinements applicable in 20% of the situations. At high cutting power; e.g., when there is an increased rate of wear due to higher temperature, the cutting time can be adjusted by a weighting coefficient determined after test results. Since the cutting temperature increases with the square of the cutting speed at the spindle, the pulse train indicative of net power is squared and the result accumulated, thereby providing a total count which determines bookkeeping and decision-making.

By combining, according to the invention, net power monitoring and computerized control, great flexibility in the system design is achieved, thereby increasing the utilization factor of cutting tools. In the past, the variety of cutting situations encountered in the shop had made it difficult to use tool monitors and machine control because of the constantly changing tool usage conditions. The present invention permits closer control of tooling, and an improved determination of the useful life of the tools before resharpening.

SUMMARY OF THE INVENTION

The invention resides in apparatus for monitoring the power applied through a tool operative on a powered machine tool comprising: first means for deriving an indication of power applied to the tool loading system of the machine when idle; second means for deriving an indication of power applied to the tool when cutting; third means for deriving an indication of net power applied to the tool by subtracting from one another the indications derived from said first and second means, and fourth means for integrating net power indication as a function of time.

Provision is made, while monitoring the power applied through said tool as a function of the derived net power indication, for limiting the cutting power within a preferred range.

The invention also resides in a method of determining the optimum life time of a tool as a function of continuous or intermittent tool use on a machine tool and by reference to a predetermined life expectancy. The method consists in integrating the net power consumed by the tool over any period of utilization and in discontinuing tool usage whenever the useful life of the tool reaches said life expectancy.

Apparatus is provided for performing the method according to the invention combining, in the operation of one or more machine tools, (1) a net power monitoring unit associated with a corresponding one of said machine tools and (2) a computerized machine control system involving one or more machine tools. The computerized control unit has the capability of integrating new power consumed by any of the tools and it records and tabulates the useful life of each and any tool by reference to respective predetermined tool life expectancies.

BRIEF DESCRIPTION OF THE DRAWINGS

FIGS. 7, 8, 9 and 10 are flow charts explaining the operation of the system of FIG. 6.

DESCRIPTION OF THE PREFERRED EMBODIMENTS

The invention is applicable to any kind of tool being operatively mounted on a machine tool, manual or automatic. Therefore it applies to cutting in general, such as drilling, milling, boring, or reaming operations, as well as to a turning operation. In either instances, a workpiece, to be shaped, contoured, surfaced or bored by taking away material in the form of chips, or otherwise, is being fed against the cutting edge of a tool with a power which depends upon the desired work and the degree of sharpness of the tool, as well as other factors such as temperature, cooling action and, in the case of a drill or mill, the speed of the spindle carrying the tool. This power applied through the workpiece, which is also the power applied through the tool is a good indication of the useful life being carved out from the life expectancy of the tool. It is also a good indication of the working conditions of the tool, e.g., whether it is too lightly applied for an effective cutting, or excessively applied which means that the tool needs resharpening. Experience tells when the proper working conditions exist, and it is necessary for an optimum tool life that the tool be used within reasonable limits of the applied power.

It has been shown (see for instance, U.S. Pat. No. 3,571,834 of Richard A. Mathias), that the speed of rotation of a cutting tool in conjunction with the feed rate of the workpiece could provide a good indication of the working conditions of the tool and help monitor its useful life, e.g., to know when it should be resharpened, or discarded.

Figure 1:
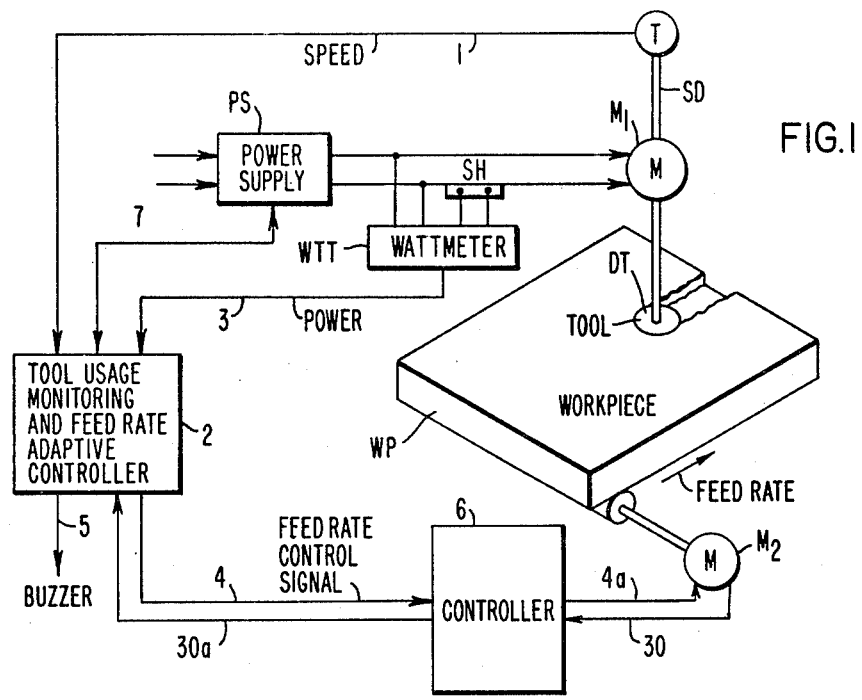
FIG. 1 schematically shows a machine tool having a tool usage monitoring system according to the present invention.

Referring to FIG. 1, a machine tool control system is shown combining indications relative to the speed of the spindle driving the tool with indications relative to the power consumed by a direct current motor $M_1$ imparting movement to a milling tool DT mounted at the end of the spindle SD. A tachometer T generates on line 1 a signal which is characteristic of the speed of the spindle SD, or the tool DT. From the power supply PS to direct current motor $M_1$, power is derived which is the product of the voltage and the armature current (indication derived from a shunt SH). In a control circuit 2, from a knowledge of spindle speed and actual power continuously recorded and compared, the operator is continuously apprised of the condition of the tool DT, e.g., when excessive power is consumed, or when sufficient power is lacking at the interface of the tool DT and the workpiece WP. Should motor $M_1$ be an induction motor, voltage, current and phase angle at the power input, will be the parameters used in ascertaining actual power actuating spindle SD. The workpiece is fed against the tool at a rate determined by a motor $M_2$ schematically shown as driving the workpiece WP. Circuit 2 automatically adjusts the feed rate by controlling from line 4 a controller 6 which is itself controlling, via line 4a, the speed of motor $M_2$. Conversely an indication of the motor speed on line 30 leads to a speed signal on line 30a to circuit 2. Still assuming motor $M_1$ is a direct current motor, from a proper relation between the speed signal on line 1 and the power signal derived on line 3, circuit 2 determines, as explained hereinafter, what the feed rate should be for an effective cutting operation. Also, circuit 2 generates on line 5 a buzzer signal which signals to the operator that cutting is no longer as it should, especially if the tool has become dull, causing burring, or not even cutting.

The difference between power under load and power at idle speed may be considered as representative of the force exerted by the tool against the workpiece. Circuit 2 of FIG. 1 first registers idle speed from line 1 and the tachometer T of motor $M_1$. Then, after the tool has been set into working position against workpiece WP, such idle speed is held as an offset to the power derived on line 3 from wattmeter WTT. Thus, any correction of the working condition can be achieved by a change in the feed rate of the workpiece, rather than in the power of motor $M_1$, which would change the idle speed, e.g., the offset. Then, adaptive control through motor $M_2$ and the feed rate can be effected independently from such working conditions of the tool. Programming of the tool operation by circuit 2 will become more reliable and easy.

Accordingly, in accordance with the present invention, the spindle speed is continuously derived and used for adaptive control, for instance, like in the aforementioned U.S. Pat. No. 3,571,834, but the idle speed will have been put aside as an offset which will be automatically changed as a function of the power applied to motor $M_1$ while the power is being changed, via line 7, by control through circuit 2 of the power supply PS of motor $M_1$.

Figure 2:
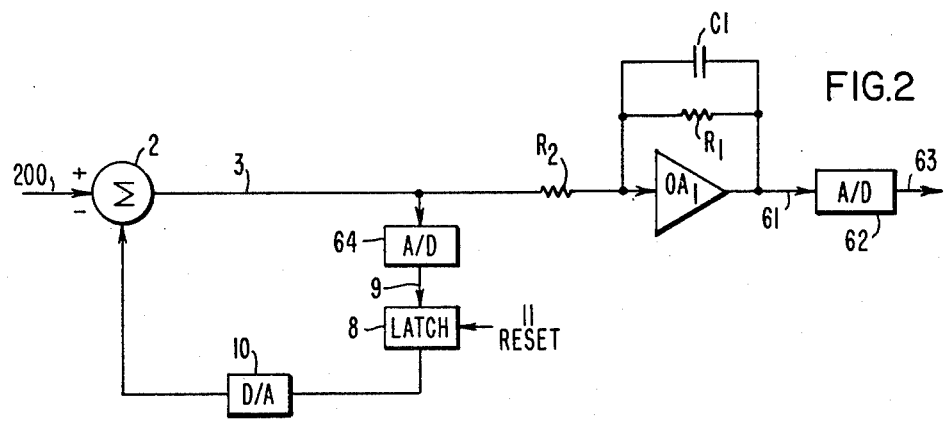
FIG. 2 shows circuit for concurrently deriving a net power indication signal in the context of the system of FIG. 1.

Referring to FIG. 2, analog circuitry is shown which within circuit 2 of FIG. 1 provides in response to power derived on line 200 an indication of net power. Assuming a spindle driven by an induction motor signal indicative of PC (power)=V (voltage)×I (current)×cos $\phi$ is derived on line 200 and applied to a summer 2. The output on line 3 normally becomes an input via a resistor $R_2$ to an operational amplifier $OA_1$ having connected between its output 5 and the input a feed-back circuit of time constant $R_1C_1$. The analog output, on line 61, is converted into a digital signal, on line 63, by A/D converter 62. Such digital data is available for treatment by a computer, relative to the tool DT, motor $M_1$ and workpiece WP (FIG. 1). According to the present invention, when spindle SD and motor $M_1$ are idle, that is when tool DT does not engage material of the workpiece WP, a certain power is derived on line 3. Under such idle conditions, the analog signal is converted by an A/D converter 64 into a digital signal appearing on line 9. This digital data is latched into latch 8 which is reset externally via line 11. The digital data so latched is then applied, after digital to analog conversion by circuit 10, as an offset onto summer 2. When under cutting operation by tool DT, power is derived on line 3 above such idle power level. Accordingly, on line 61, instead of total power, digital data representing net power is being constantly monitored. Under different cutting operations, by line 11, the latched value in latch 8 is brought back to zero, so that another offset value can be derived each time a new cutting operation is being initiated.

Figure 3:
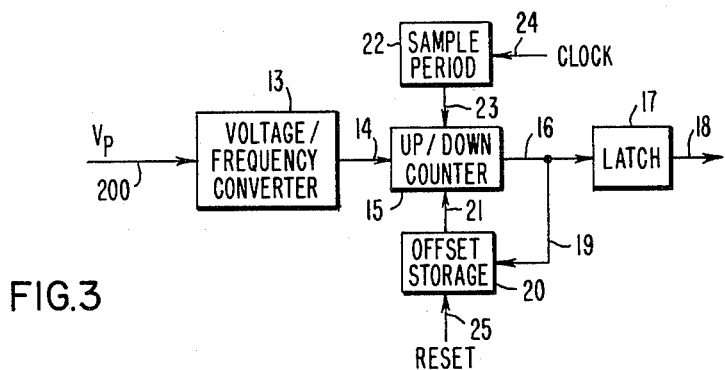
FIG. 3 is a digital circuitry for a net power monitor unit that can be used in accordance with the present invention.

Referring to FIG. 3, digital circuitry is shown for the same purpose as in FIG. 2. The analog signal representing power on line 200 is converted by circuit 13 into a pulse train having a frequency rate which is proportional to the magnitude of signal $V_P$ on line 200. Circuit 13 may be a voltage controlled oscillator, as generally known. Within a sampling period defined by circuit 22, clocked by line 24, an up/down digital counter 15 counts so many pulses. Such count is latched at 17 and used, by line 18, as digital data, for instance by a computer. Again, during idle conditions, the count derived on line 16 is derived via line 14 and stored into an offset storage circuit 20. The offset is applied as a down count, thus subtracted from the up count which is constantly derived during every sample period of line 23. Thus, a net power indication is obtained in latch 17 and at the output 18.

Figure 4:
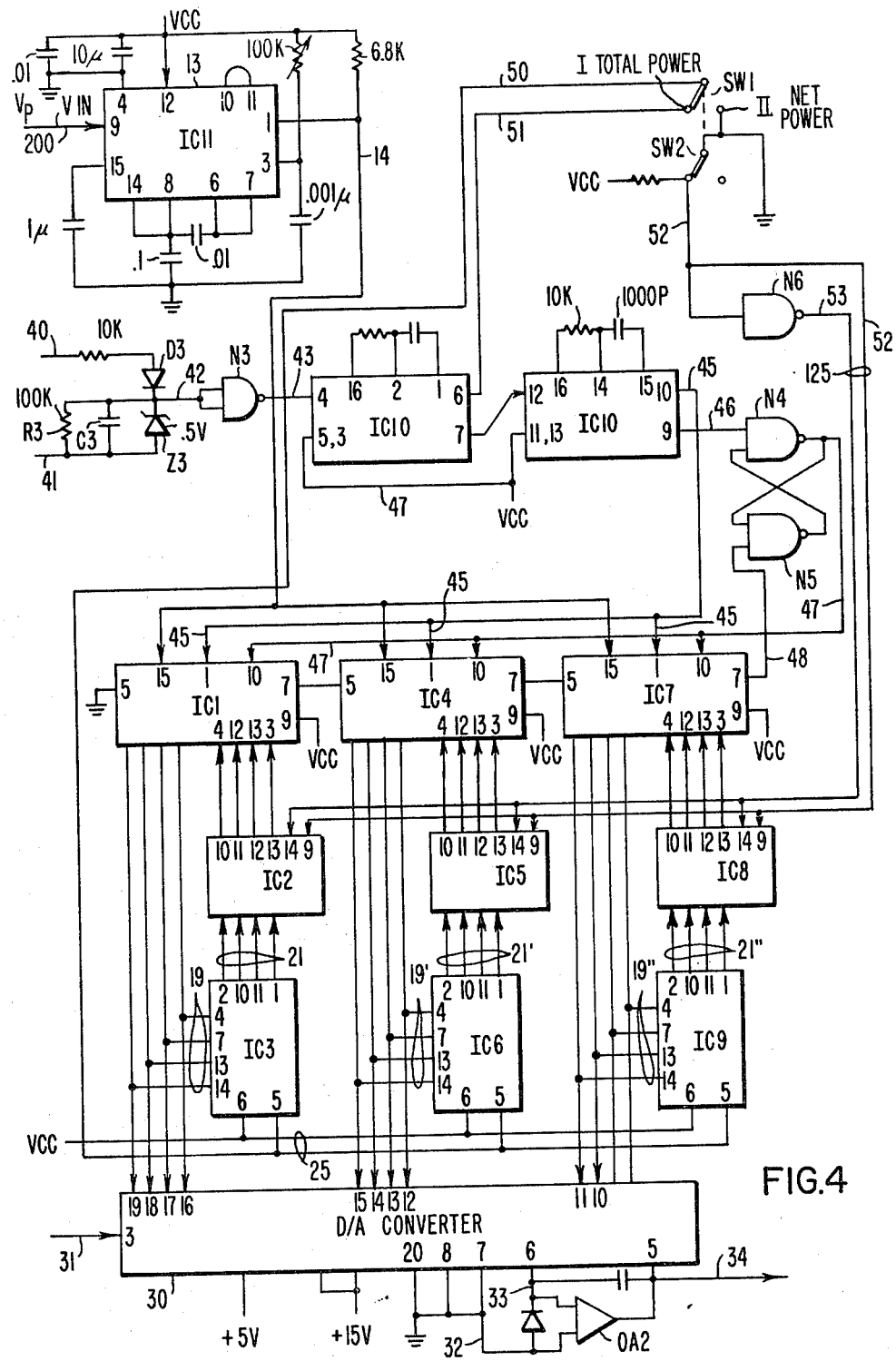
FIG. 4 is a more detailed digital circuit for the net power monitor unit of FIG. 3.

Referring to FIG. 4, digital circuitry for deriving an indication of net power in response to a voltage signal $V_P$ from line 200, is provided as an illustration of one particular embodiment in an alternative form of the invention shown in FIG. 3.

The voltage-to-frequency converter 13 of FIG. 4 is built around a solid state device sold on the market by INTECH under the code name A-8402. The voltage input on pin 9 appears, on pin 1 and line 14, as an output pulse train. The pulse train of line 14 is applied to a counter 15 in the form of three solid state devices $IC_1$, $IC_4$ and $IC_7$ sold on the market under the code name CD 4029. The successive pulses received on pins 15 are converted into a digital count on pins 6, 11, 14 and 2 of the respective solid state devices on the counter. Only ten bits are used to represent the digital count, namely 4 bits on lines 16, 4 bits on line 16' and 2 bits in lines 16" from $IC_1$, $IC_4$, and $IC_7$, respectively. A 10 bit multiplying digital-to-analog converter (DAC) 30 provides between its pins 7 and 6 an analog signal which is inputted between the inverting and non-inverting inputs of an operational amplifier $OA_2$ outputting, on line 34, an output signal corresponding to the signal of line 18 in FIG. 3. The gain of D/A converter 30 is determined by a control signal applied on pin 3, from line 31 in the process.

The sampling circuit 22 of FIG. 3, appears in FIG. 4 as a circuit built around two solid state devices IC10. This circuit is in the form of two half CD4098 devices and a flip flop $N_4/N_5$. A 60 hertz signal applied between lines 40, 41 triggers an oscillating circuit comprising resistor $R_3$ and capacitor $C_3$. As a result, a logical input developed at the junction between diode $D_3$ and zener diode $Z_3$ is inputted into NOR device $N_3$ which in turn triggers, via pin 4, the first solid state device IC10. A 10K resistor between pins 16 and 2 and a 1000P capacitor between pins 2 and 1 together establish a time interval between alternate Q states of solid state devices IC10 on pins 7 and 9 thereof, with the Q state on pins 6 and 10.

Accordingly, flip-flop $N_4/N_5$ generates an analog signal on line 47 leading to pins 10 of the three elements $IC_1$, $IC_4$, and $IC_7$ forming up/down counter 15, while the transfer signal is received from pin 10 of solid state device IC10 and applied by line 45 onto pins 1 of solid state devices $IC_1$, $IC_4$, and $IC_7$.

Switches $SW_1$ and $SW_2$ may assume two possible positions I and II. FIG. 4 shows switches $SW_1$ $SW_2$ in the position I. In such case, the oscillator built around solid state devices IC10 provides on its pin 6 a logic pulse at the sampling rate, which by lines 51 and 50 ($SW_1$ closed) constantly enables latches $IC_3$, $IC_6$ and $IC_9$ by its pin 5, thus, causing the devices to continuously be reset without latching any offset into $IC_3$, $IC_6$ and $IC_9$. At the same time the count on lines 16, 16', and 16" is continuously updated.

When power for idle spindle speed is to be taken as an offset, switches $SW_1$, $SW_2$ are in position II. The count outputted on lines 16, 16' and 16", also appears on lines 19, 19' and 19" as an input to respective solid state devices $IC_3$, $IC_6$, and $IC_9$. Switch $SW_1$, being to ground at position II, devices $IC_3$, $IC_6$ and $IC_9$ latch the digital value appearing on lines 19, 19', and 19". Such stored count is the offset referred to in block 20 of FIG. 3. This offset is then applied by lines 21 concurrently to the solid state devices $IC_2$, $IC_5$ and $IC_8$. As a result of $SW_2$ being in position II, $V_{CC}$ via line 52, device $N_6$ and lines 125 on pins 14, 9, enables $IC_2$, $IC_5$ and $IC_8$. Then the offset appears as a subtrahend on lines 121, 121', and 121" to pins 4, 12, 13 and 3 of the three solid state devices $IC_1$, $IC_4$ and $IC_7$ forming counter 15. Therefore, when the tool is in operation and material from the workpiece is being taken away, with switches $SW_1$, $SW_2$ in position I the clock on lines 45 causes on pins 6, 11, 14, and 2 the net count to appear. This digital net power signal can then be stored and/or used. This count is converted into a net power indicative signal after conversion into an analog signal by D/A converter device 30, and outputted by operational amplifier $OA_2$ on line 34.

Figure 5:
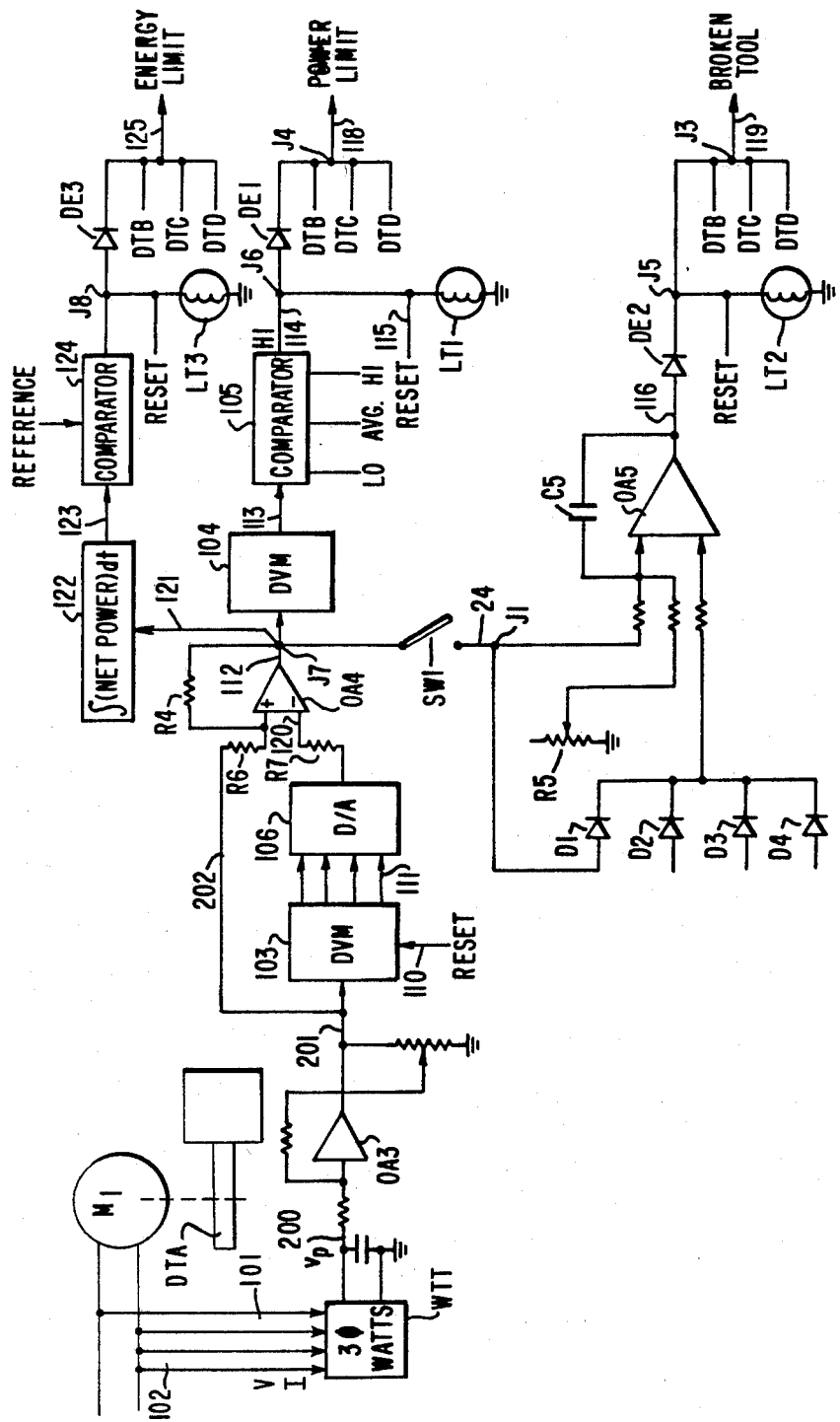
FIG. 5 is a net power and energy monitoring system adapted for multi-tool monitoring and warning in accordance with the present invention.

Referring to FIG. 5, a net power monitoring system is shown applied to a multiple-tool control machine system. Typically, four spindles $SD_1$, $SD_2$, $SD_3$ and $SD_4$ carrying tools DTA, DTB, DTC and DTD and driven by individual motors $M_1$, $M_1'$, $M_1''$ and $M_1'''$, are each operative within an individual tool monitoring channel. The tool monitoring channel relative to tool DTA is illustratively shown in FIG. 5.

Considering the illustrated channel, a wattmeter WTT is responsive to a voltage signal input 101 and a current signal input 102 for providing a continuous analog signal on output line 200 representing instantaneous power $V_p$. Signal $V_P$ is passed through a preamplifier in the form of an operational amplifier $OA_3$, outputting on line 201 a signal which is normally representative of actual torque on spindle $SD_1$. Motor $M_1$ driving spindle $SD_1$ in this embodiment is a three-phase motor of 5 horse-power operative at a frequency varying from 20 to 120 Hz.

The signal of line 201 is first applied into the input of a digital voltmeter (DVM) 103, e.g. into a circuit outputting on lines 111, a several bit digital representation of the inputted analog signal. Secondly, the signal is applied via line 202 to the inverting input of an operational amplifier $OA_4$. Circuit 103 has the capability of latching the information received until reset externally by line 110. The outputted and latched digital signal of lines 111 is converted into an analog signal by digital-toanalog converter (D/A) circuit 106. The converted signal appearing on line 120 is applied to the non-inverting input of operational amplifier OA4 the output of which from a junction point J7 is fed into another digital voltmeter 104. It is the property of a digital voltmeter (DVM) such as circuit 104 to operate under its own cycle, for instance every halfsecond, to latch the received input value, and stay in this state until reset internally. From a consideration of the explanations already given in relation to FIG. 2 or 3, it will be understood that when, initially, tool DTA is not applied against the workpiece WP, e.g. when motor $M_1$ only works with idle power, the analog signal of line 201 will cause a latched digital signal to appear on lines 111 and keep such latched value as an input, on line 120, of operational amplifier OA4. Thus, when tool DTA is cutting, actual power is indicated on line 202. At this time, by the operation of operational amplifier OA4 net power (actual power shown on line 202 less the power shown on line 120), is derived at the output 112 of operational amplifier OA4.

The net power signal of line 112 is applied from junction J7 to digital voltmeter 104 (which is not resetable externally), to display the current net power indication. A comparator 105 having two thresholds LO for "low" and HI for "high" and a middle level AV for "average", indicates whether the net power is below, or between two upper and lower values which are considered critical for the particular operation of the particular tool DTA. Thus, limit LO corresponds, for instance, to an excessively light cut, whereas HI corresponds to an excessively high cut. In one instance, the tool may have broken, in the second alternative it runs the risk of breaking. These three possible types of information are recorded, or displayed, in accordance with the status of comparator 105. Moreover, the output of line 114 from comparator 105 is passed through a rectifier $DE_1$ onto a junction $J_4$, common to all four channels, which is connected to a common buzzer actuated from line 118 whenever comparator 105, or any of the similar comparators of the other channels, is high (HI). A light $LT_1$ is actuated from junction $J_6$, on line 114, to indicate such extreme value of the net power signal on line 113 e.g. "net power>Power Limit". Light $LT_1$ is resetable from line 115.

The signal of line 112 is also passed from junction $J_7$ to a junction $J_1$ common to all channels, whenever a switch $SW_3$ is being closed. Junction $J_1$ is inputted into one input of operational amplifier $OA_5$ which is the integrating input from a feed-back loop including a capacitor $C_5$. Junction $J_1$ is also connected, via a diode $D_1$, to a junction $J_2$ common to all channels, thus, after respective diodes $D_1$, $D_2$, $D_3$ and $D_4$. Junction $J_2$ goes to the second input of operational amplifier $OA_5$. The feedback loop of integrator $OA_5$ is connected to the moving arm of a potentiometer $R_5$ mounted between a reference potential and ground. The output of operational amplifier $OA_5$ on line 116 goes a junction point $J_5$ and to a diode $DE_2$. From there, the voltage is applied first to a light $LT_2$ connected to ground, secondly to another buzzer on line 119 via a junction $J_3$, also common to all channels.

It appears that, when the net power signal on line 112 maintains a low value during a minimum time duration defined by the time basis $C_5 R_5$ of the integrator feedback via capacitor $C_5$, the output of operational amplifier $OA_5$ is indicative of a broken tool. Resistor $R_5$ can be adjusted in order to set the deviation allowed from the normal amplitude of the net power signal on line 112 until it will cause the output of $OA_5$ to reach the critical level. For each critical level, diode $DE_2$ breaks down, thereby actuating alarm light $LT_2$ and the buzzer which beyond junction $J_3$ on line 119 is common to all the channels.

From junction $J_7$, via line 121 the net power indication signal is applied to an integrator 122 effectuating the integration $\int$ (net power)$_{dt}$, as earlier stated by reference to equation (2). As a result, at the output 123 a signal is derived representing the energy consumed by tool DTA. This is in contrast with the information on line 113 which is indicative of net power applied when the tool engages the workpiece in the cutting operation. Like for the signal of line 113, the signal of line 123 is applied at the input of a comparator 124 having a predetermined reference provided externally. When the threshold of comparator 124 is exceeded, at junction $J_8$ a condition is fulfilled for actuating a resettable light $LT_3$, and for causing breakdown of a diode $DE_3$ whereby on line 125 a buzzer is actuated. Thus, on line 125 and with light $LT_3$, the circuit of FIG. 5 permits the detection of excessive energy being reached with tool DTA (or tools DTB, DTC, DTD for the other channels), e.g. "energy>energy limit".

The gist of the present invention lies in being able to distinguish the extent of net power consumed with the tool up to a certain upper limit (HI) from the extent of energy consumed with the tool up to a certain upper limit (HI). In the first instance, a control system is provided which is able to detect an excessive force being applied to the tool, thus a conduction of impending breakdown. In the second instance, the control system detects in a continuous or intermittent fashion the degree of wear of a particular tool, which results in being able to detect when a predetermined "energy limit" has been reached, or exceeded, e.g. the optimum use of the tool, at which time it is opportune to change the tool. Also, as shown by FIG. 5, the control system according to the present invention provides the ability of detecting when the tool has become, actually, broken.

Figure 6:
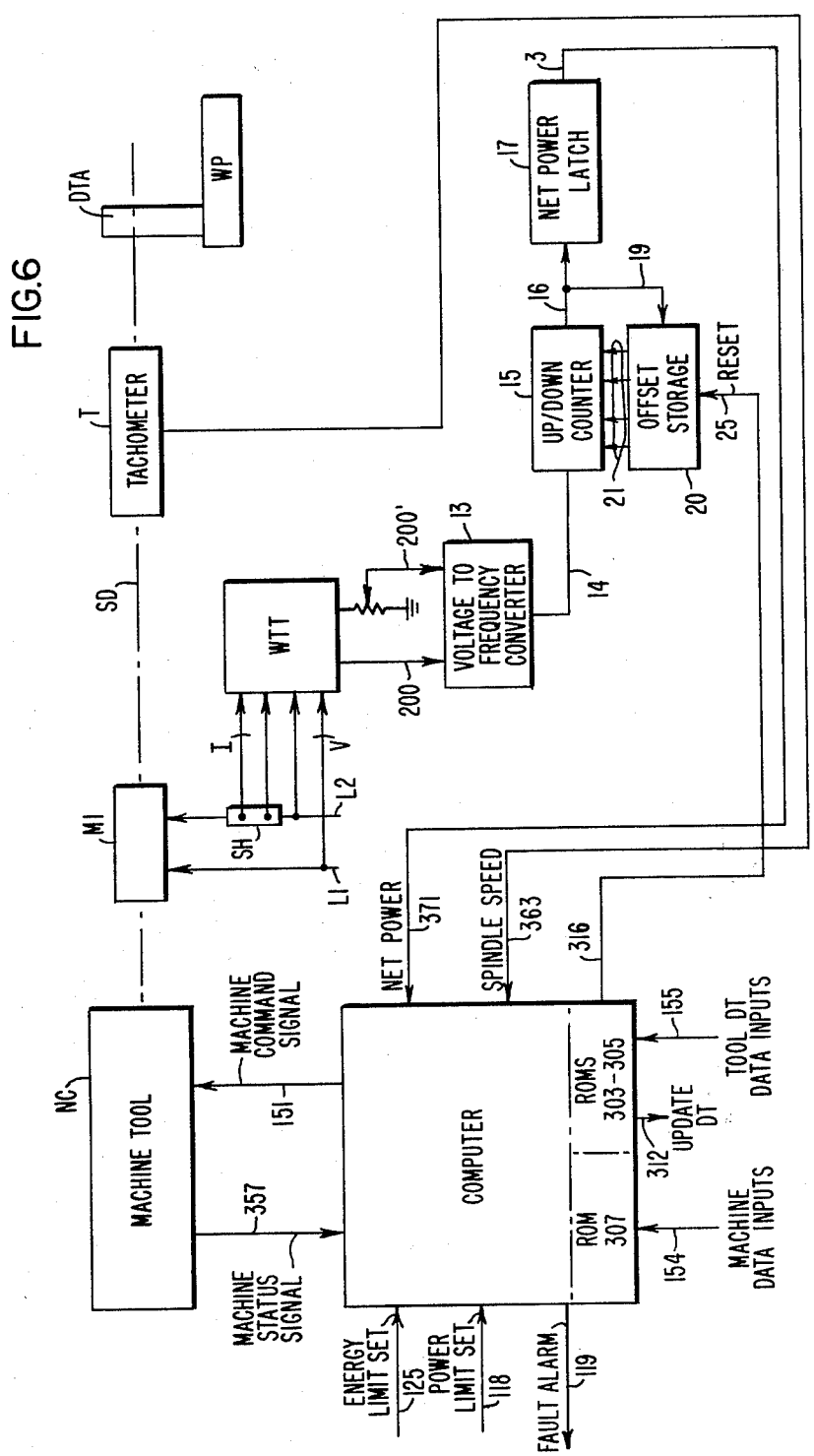
FIG. 6 is a schematic view of a machine tool installation combining net power monitoring and computerized numerical control in a preferred embodiment of the invention.

Referring to FIG. 6, the preferred embodiment of the invention is schematically shown to include a machine tool controlled by a computer. DC motor $M_1$ driving the spindle SD of the machine tool is supplied with electrical energy from lead lines $L_1$ and $L_2$ having a shunt SH for deriving an indication of current I and a wattmeter WTT is supplied with indications of the current I and the voltage V for providing on lines 200, 200' a voltage signal indicative of instantaneous power. A voltage to frequency converter 13 generates on line 14 a pulse train having a pulse rate determined by the magnitude of the inputted voltage signal. Spindle SD actuates a tachometer T used to derive on line 1 an indication of the spindle speed. Spindle SD sets in motion a tool DTA in working relation with a workpiece WP as determined by the machine tool. FIG. 6 is only illustrative. Thus, DTA is illustrated as a tool rotating about the axis of the spindle SD and engaging a workpiece WP. It is not shown how relative displacement is effectuated between the tool and the workpiece between an idle position and a working position. Material feed control is not shown. However, these techniques are generally known and can easily be understood by anyone skilled in the art of machine tools. It is also clear that if the machine tool is a lathe, the tool will be positioned against a rotating workpiece WP instead of the converse as shown in FIG. 6.

An up/down counter 15 is provided responsive to the pulse train of line 14 to output on line 16 a counter which is representative of the accumulated power totalized by wattmeter WTT, e.g. of the total power supplied to motor $M_1$ in rotation. If the tool is away from the workpiece, thus is doing no work, spindle SD is said to be idle, and the power demand on motor $M_1$ is at a minimum. Under such condition, the count on line 16, which is also applied on line 19 into an offset storage device 20, is latched therein. When tool DTA is positioned so as to cut material from workpiece WP, the power demand of motor $M_1$ is increased, and the pulse train of line 14 appears with a higher pulse rate. The offset from device 20 is via line 21 automatically subtracted from the current count into counter 15. Thus, as earlier explained by reference to FIG. 3, counter 15 is supplying on line 16 the net power demand of motor $M_1$, e.g., the work done by tool DTA. Circuit 17 latches net power as applied on line 16. In accordance with afore-stated equation (2) and as explained. hereinafter a computer associated with the machine tool provides in response to line 3 the integral, as a function of time, of net power in relation to the operation of tool DTA.

As generally known, the computer may be part of the machine tool to form a numerical control computerized machine. It is also possible that the numerical control machine is placed as OEM on the site, alone, or in parallel with other machines while a centrally located computer determines the operation of all the OEM machine tools individually under a common executive program. For the sake of clarity, FIG. 6 shows only a computer and one machine tool. As explained by reference to FIG. 5, the invention provides for continuous as well as intermittent use of one or more tools such as DTA, DTB, DTC, etc. When one tool has accumulated what is considered its normal life expectancy, the tool is changed and another one is set in place. Also, if a tool is changed before its full use, it is put aside, but its remaining life is known and its amount set apart on record so that it can be used again up to the end of its life expectancy. The computer monitors the actual life of any or all tools, by tabulating the amount and level of activity of the tool.

Integrated net power, which according to the present invention is the main parameter for monitoring the life expectancy of a tool such as DTA in FIG. 6, is derived by the computer. The computer is also informed of the spindle speed by line 1 and 363. The computer controls the machine tool by imparting via lines 151 machine command signals to the machine tool in relation to machine status signals received on line 357. The operator ascribes to the system machine data inputs by line 154 into the computer, and sets all the data relevant to each or any tool such as DTA by lines 155 into the computer. The computer also resets by lines 316, 25 the offset storage device whenever a new idle speed condition requires a new offset. The limits known to be exceeded, or fault conditions detected, by lines 118, 119, and 125 of FIG. 5 are also known to the computer.

The operation of the tool monitoring apparatus of FIG. 6 will now be explained through flow charts which are provided for the purpose of illustration only, as follows:

First, in the computer are stored data relative to the tools in use or to be used in accordance with the tables herebelow:

TABLE I

Tool Style Data

Tool Type
Usage (Cutting) Time Limit
Net Power Limit
Total Energy Limit
Times Used Limit (When Applicable)

TABLE II

Individual Tool Data

Figure 7:
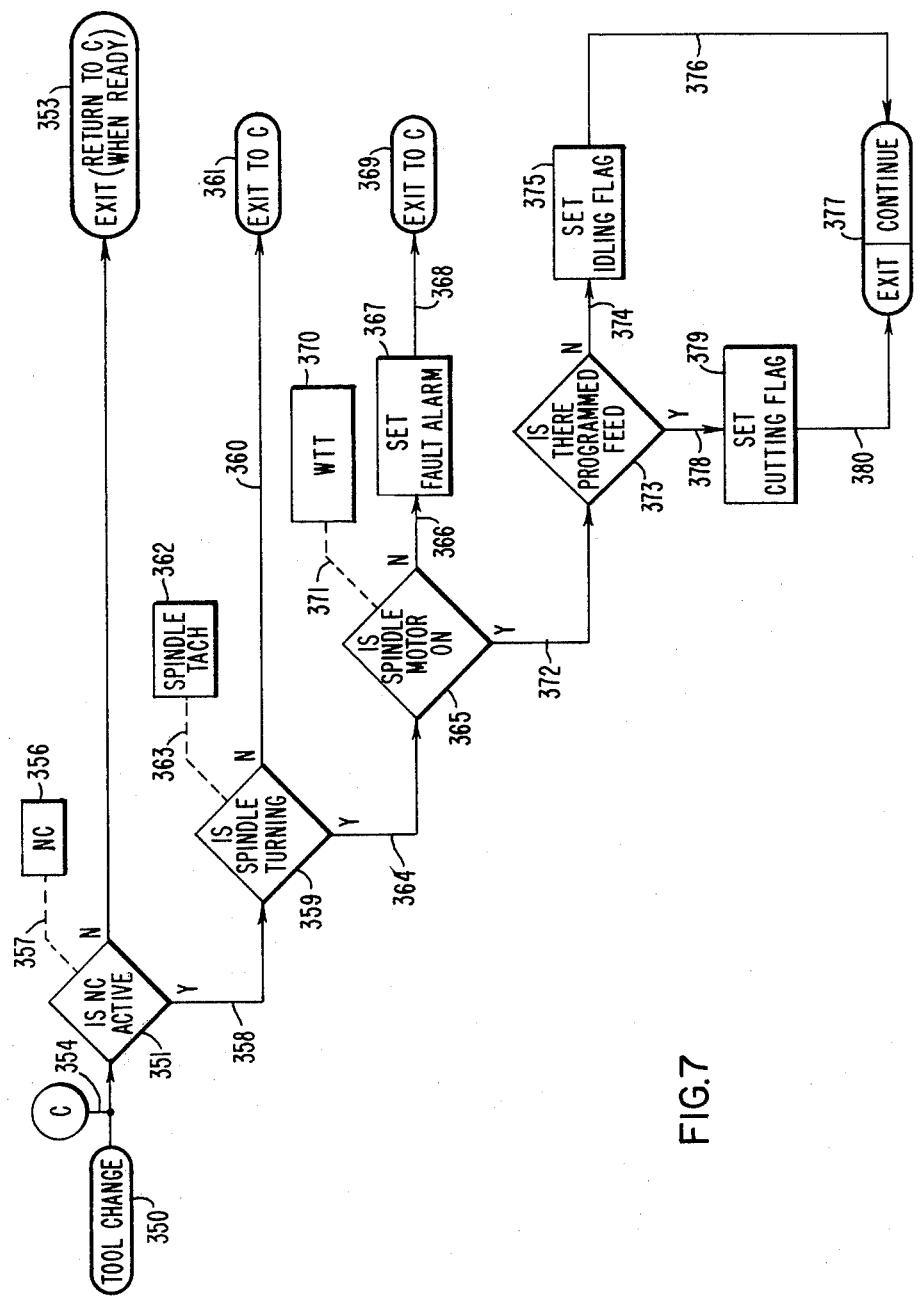

Tool Style
Tool Number (DTA)
Times Used
Accumulated Usage (Cutting) Time
Maximum Net Power
Accumulated Energy Consumed
Time Used Exceeding Net Power Limit
Time Used Exceeding Energy Power Limit
Time Used Exceeding Usage Time Limit Referring to FIG. 7, is a flow chart illustrating the subroutine followed after the changing of a tool (at 350). The system first determines whether the machine tool NC is active or not (at 351). This is ascertained from line 357 by a status signal (FIG. 6). If the machine tool is not active (NO at 352), the subroutine exits (at 353) and the question by C (on line 354) is asked again, until the answer on line 358 from block 351 is YES. Then, the system asks at 359 whether the spindle is turning. This is ascertained by the indication received from the spindle tachometer on line 1, 363. If the answer at 360 is NO, the system at 361 goes back to C (by 354) and to 351. If the answer is YES, the question becomes whether the spindle motor $M_1$ is ON (at 365). This is known from the net power output on line 3, 371. If the answer is NO, this being contradictory with the YES answer on line 364, the system by line 366 sets a fault alarm at block 367, then, goes back to C by block 369 and line 354. If the answer is YES, (line 372) the question becomes "Is there a programmed feed" (block 373). At this point, the system goes either by line 378 to block 379, commanding to set the cutting flag, or by line 374 to block 375 commanding to set the idling flag. As explained by reference to FIG. 6, counter 15 feeds back into offset storage device 20, when the idling flag is ON, so that the system provides the offset value. When the cutting flag is on, net power is derived on line 16 at the output of counter 15. In either instance, the subroutine of FIG. 7 terminates. If "idling" the system continues, if "cutting" the system exits.

Referring to FIG. 8, the main flow chart of the overall operation of the monitoring system according to the preferred embodiment of the invention is illustrated.

Starting at A, by line 328, the system goes to 350 which indicates that a tool change has physically occurred. After a tool change the system goes to block 302 for initializing the tool style use limits, in accordance with Table 1 (303 being the ROM device which in the computer contains data from Table I). When this is completed, in block 304 the system initializes the storage of cumulative tool usage data which in ROM device 305 of the computer is stored in accordance with Table II. Then by line 327 the flow chart leads into block 306. The system makes a review of the machine status as shown by line 357, as well as by the net power input of line 371 and the spindle speed signal of line 363 as illustrated by the subroutine of FIG. 7 (see also the inputs to the computer on FIG. 6). Other possible inputs are the feedrates on line 388. The system comes thereafter, at block 308 with the question "Is a new tool needed?" If the answer is YES, by line 309 and block 311, the system goes to register 305, e.g., Table II, for updating of the individual tool data. Then, at block 313 the flag indicating tool replacement is set, and the system goes back to 328 by block 331.

If, however, the answer at block 308 is "NO" (by line 310), the system goes to the question of block 315: "Is the machine idling?", which is preliminary to taking and latching the offset value of device 20 (FIG. 6). Thus, if the answer is YES (by line 316), the offset storage device 20 is reset (block 329) and the system by line 317 and block 330 exits going back to line 327 and block 306. This means that the spindle speed from line 363 will be ascertained, namely idle speed, as well as the other status signals of lines 357, 388. When the answer to block 315 is NO, (by line 318), the net power count derived on line 3,371 is integrated and accumulated on the basis of prior history.

This operation is explained by the subroutine of FIG. 9. Since the answer on line 318 is NO (FIG. 8), the system is in the "machine cutting" condition (initial block 400 of FIG. 9). The question becomes, "Is net power larger than the previous maximum?" (block 401). If the answer is YES, (by line 402), according to block 403 the maximum net power is updated, and by line 404, the system goes to line 405 which is the position when the answer to block 401 is NO.

From line 405, the system goes to updating the usage time and the energy used for the particular tool (DTA). See block 406. When this has been done, the subroutine ends by line 407 and block 408. Then, and on the main flow chart of FIG. 8, the question, as stated in block 321 becomes "Are any limits exceeded?". These questions are spelled out in the flow chart of FIG. 10. The total limit check (block 450) is effected from line 451 first by answering the question of block 452, whether net power exceeds the preset power limit. If the answer is YES, (by line 453) in block 454 the conclusion is that the increment time limit has been exceeded and by block 455 the alarm flags are set, namely, (1) immediate stop; (2) end of cut, stop; and (3) tool change, stop. The system returns by line 456 to the NO output (line 457) of block 452.

From line 457, or line 457, the next question is "whether the total energy used up by the tool exceeds a preset energy limit" (block 458). If the answer is YES, by line 459 it is concluded in block 460 that the increment time limit has been exceeded and in block 461, the above stated alarm flags 2 or 3 are set. Then, the system by line 462 goe to the NO answer of line 463 to the question of block 458. Now, the question is whether the usage time is larger than the time limit. If the answer is YES (at line 465), the conclusion of block 466 is again that the increment time limit has been exceeded. It follows that alarm flags 2 or 3 are set according to block 468 and the system goes to the NO answer of line 470 from block 464. Thereafter, on the main flow chart of FIG. 8, the system is at B on lines 326 and 327 as before. Block 321 and block 323, of FIG. 8, provide a simple representation of the subroutine of FIG. 10. The output line 324 (via block 325) corresponds to the return to point B at lines 326 and 327 of the main flow chart.

We claim:

1. A system for monitoring tool life on a machine tool having at least one operative tool thereon, comprising:
    means for instantaneously and recurrently deriving a measuring signal characteristic of power consumed by said machine tool for the purpose of relative motion between said workpiece and said tool;
    said measuring signal deriving means being operable in one of an idle position mode and a working position mode of said tool relative to said workpiece;
    means for combining an idle position measuring signal and a working position measuring signal for deriving a signal indicative of net power consumed by said tool;
    means for integrating said indicative signal as a function of time for obtaining a past history characteristic signal;
    means responsive to said integrating means for comparing said characteristic signal with a reference signal representative of the life expectancy of said tool.

2. The system of claim 1 with said measuring signal deriving means comprising voltage to frequency converter means for providing a pulse train having a pulse rate characteristic of said measuring signal;
    counter means for counting pulses in said pulse train during a sample time interval, and offset storage means operative to store a count from said counter means when in the idle position mode;
    said combining means being operable to subtract said idle position count from a count derived from said counter means in the working position mode.

3. The system of claim 2 with means responsive to said power signal indicative means and to a predetermined maximum net power limit for setting an alarm when said net power limit is exceeded.

4. The system of claim 3 with said alarm setting being effective when said net power limit has been exceeded during a predetermined minimum time interval.

5. The system of claim 2 with means responsive to said comparing means for providing a command signal for changing said tool when the threshold of said reference signal has been reached by said life status signal.

6. The system of claim 5 with means responsive to said integrating means for providing an indication of excessive energy being used with said tool.

7. The system of claim 5 with means for storing an indication of said life status signal operative after and before an interruption in the use of said tool.

* * * * *